US012577525B2

(12) United States Patent
Treier-Marxen et al.

(10) Patent No.: US 12,577,525 B2
(45) **Date of Patent: \*Mar. 17, 2026**

(54) METHOD OF PURIFYING A PROTEIN FROM FERMENTATION SOLIDS UNDER DESORBING CONDITIONS

(71) Applicant: BASF SE, Ludwigshafen (DE)

(72) Inventors: Katrin Treier-Marxen, Ludwigshafen (DE); Petra Deckert, Bammental (DE); Andreas Schaedler, Weyher (DE); Vaidotas Navickas, Mannheim (DE); Volker Wengert, Worms (DE); Thomas Kaeding, Lampertheim (DE)

(73) Assignee: BASF SE, Ludwigshafen (DE)

( \* ) Notice: Subject to any disclaimer, the term of this patent is extended or adjusted under 35 U.S.C. 154(b) by 0 days.

This patent is subject to a terminal disclaimer.

(21) Appl. No.: 18/443,753

(22) Filed: Feb. 16, 2024

(65) Prior Publication Data

US 2024/0191175 A1      Jun. 13, 2024

Related U.S. Application Data

(63) Continuation of application No. 16/060,626, filed as application No. PCT/EP2016/080165 on Dec. 8, 2016.

(30) Foreign Application Priority Data

Dec. 9, 2015     (EP) ..................................... 15198622

(51) Int. Cl.
| | |
|---|---|
| *C12N 1/02* | (2006.01) |
| *B01D 61/14* | (2006.01) |
| *B01D 61/16* | (2006.01) |
| *C07K 1/14* | (2006.01) |
| *C07K 1/30* | (2006.01) |
| *C12P 21/02* | (2006.01) |

(52) U.S. Cl.
CPC ............. *C12N 1/02* (2013.01); *B01D 61/147* (2013.01); *B01D 61/16* (2013.01); *C07K 1/145* (2013.01); *C07K 1/30* (2013.01); *C12P 21/02* (2013.01); *B01D 2311/04* (2013.01); *B01D 2311/18* (2013.01); *B01D 2315/16* (2013.01)

(58) Field of Classification Search
CPC ........ C12N 1/02; B01D 61/147; B01D 61/16; B01D 2311/04; B01D 2311/18; B01D 2315/16; C07K 1/145; C07K 1/30; C12P 21/02
USPC ....................................................... 435/325
See application file for complete search history.

(56) References Cited

U.S. PATENT DOCUMENTS

| | | | |
|---|---|---|---|
| 4,379,844 A * | 4/1983 | Young ................... | A23K 10/12 |
| | | | 435/911 |
| 6,582,606 B2 | 6/2003 | Laustsen et al. | |
| 6,866,782 B2 | 3/2005 | Scapol et al. | |
| 8,420,789 B2 | 4/2013 | Takeda et al. | |
| 2019/0024038 A1 | 1/2019 | Treier-Marxen et al. | |

FOREIGN PATENT DOCUMENTS

| | | |
|---|---|---|
| CN | 1213376 A | 4/1999 |
| CN | 101368177 A | 2/2009 |
| DE | 102012215642 A1 | 3/2014 |
| EP | 1273592 A2 | 1/2003 |
| EP | 1561756 A1 | 8/2005 |
| WO | WO-00/43502 A1 | 7/2000 |
| WO | WO-01/87468 A1 | 11/2001 |
| WO | WO-02/055537 A1 | 7/2002 |
| WO | WO-2008/110498 A1 | 9/2008 |
| WO | WO-2011/003784 A1 | 1/2011 |

OTHER PUBLICATIONS

Avwioroko et al., Isolation, identification and in silico analysis of alpha-amylase gene of Aspergillus niger strain CSA35 obtained from cassava undergoing spoilage, Biochem. Biophys. Rep., 14:35-42 (2018).

Bossi et al., Focusing of alkaline proteases (subtilisins) in pH 10-12 immobilized gradients, Electrophoresis, 15(12):1535-40 (1994).

European patent application No. 15198622.1, Extended European Search Report, dated Apr. 25, 2016.

International Application No. PCT/EP2016/080165, International Preliminary Report on Patentability (Chapter II), dated Mar. 29, 2018.

International Application No. PCT/EP2016/080165, International Search Report and Written Opinion, mailed Jan. 30, 2017.

Kobayashi et al., Purification and properties of an alkaline protease from alkalophilic *Bacillus* sp. KSM-K16, Appl. Microbiol. Biotechnol., 43(3):473-81 (1995).

Pall, PallSep™ Systems, downloaded from the Internet at: <http://shop.pall.com/us/en/biotech/tangential-flow-filtration/automated-systems/pallsep-systems-zidgri781fv> (2019).

Subtilisin, Wikipedia entry, downloaded from the Internet at: <http://www.en.wikipedia.org/wiki/Subtilisn> (2019).

\* cited by examiner

*Primary Examiner* — Jennifer M.H. Tichy

(74) *Attorney, Agent, or Firm* — MARSHALL, GERSTEIN & BORUN LLP

(57) ABSTRACT

The present invention is directed to a method of purifying a protein of interest from the particulate matter of a fermentation broth comprising the step of purifying the protein of interest from the particulate matter of the fermentation broth, wherein the step of purifying the protein of interest from the particulate matter of the fermentation broth comprises one or more washing steps, which comprises contacting the particulate matter with a washing solution comprising one or more conditions that favor the solubilization of the protein of interest and/or the desorption of the protein of interest from the particulate matter.

20 Claims, No Drawings

METHOD OF PURIFYING A PROTEIN FROM FERMENTATION SOLIDS UNDER DESORBING CONDITIONS

CROSS-REFERENCE TO RELATED APPLICATIONS

This application is a continuation of U.S. patent application Ser. No. 16/060,626, which is a U.S. National Stage application of International Application No. PCT/EP2016/080165, filed Dec. 8, 2016, which claims priority to European Patent Application No. 15198622.1, filed on Dec. 9, 2015. The aforementioned applications are hereby incorporated herein by reference in their entireties.

FIELD OF THE INVENTION

The present invention is directed to a method of purifying a protein of interest from the particulate matter of a fermentation broth comprising the step of purifying the protein of interest from the particulate matter of the fermentation broth, wherein the step of purifying the protein of interest from the particulate matter of the fermentation broth comprises one or more washing steps, which comprises contacting the particulate matter with a washing solution comprising one or more conditions that favor the solubilization of the protein of interest and/or the desorption of the protein of interest from the particulate matter.

BACKGROUND OF THE INVENTION

The biotechnological production of useful substances by cultivation of selected microorganisms producing these substances is now of considerable industrial significance. Especially, the industrial production of proteins, in particular washing- and/or cleaning-active enzymes, but also pharmacologically active proteins, by fermentation has increased over the past decades.

For the fermentation product to be incorporated into commercial products purification from the particulate matter of the fermentation broth after completion of the fermentation process is usually required. However, recovery of the fermentation product, especially recovery of a protein of interest, from the culture broth is often hampered by the fact that a significant amount of the fermentation product is not in a solubilized form and adheres to the particulate matter in the fermentation broth resulting in significant yield losses.

Various methods exist in the art to improve solubility of the protein of interest and to reduce binding of the protein of interest to the particulate matter, in particular the biomass, in the fermentation broth.

In U.S. Pat. No. 6,582,606 a purification method is described comprising the adjustment of the fermentation broth comprising a savinase to pH 5.2 and the addition of CaCl2) and activated carbon subsequent to a 100% dilution of the fermentation broth. The bacterial cells were removed by subsequent simple microfiltration.

WO2011003784 discloses a method for purifying an amylase or a protease from a fermentation broth by adjusting the pH of the fermentation broth to pH 6.5-pH 10.5 subsequent to a 600% dilution of the fermentation broth and the addition of CaCl2 and sodium phosphate. Bacterial cells are described to be separated by subsequent centrifugation. As an additional means to process the protein solution after removal of the cells WO2011003784 suggest further purification for instance by means of ultrafiltration, diafiltration, extraction, spray-drying, evaporation, precipitation or crystallization.

In WO0043502A2 a method for recovering a glycosidase or a peptidase from a culture broth is disclosed comprising the step of adjusting the pH of the culture broth prior removal of the cells to a pH value between about 9.5 and about 13. In WO0043502A2 the purification of an amylase is described, wherein a sample of the culture broth is diluted 200% (w/w) with water, supplemented with a flocculant and the pH of the sample is adjusted to pH 10.5. Subsequently, the biomass is removed by centrifugation and the amylase activity in the supernatant was determined to be 80% compared to the enzyme activity in the fermentation broth prior enzyme purification.

WO2008110498A1 describes a method of solubilizing protease crystals and/or protease precipitate in a fermentation broth. In WO2008110498A1 a subtilisin protease is solubilized by applying the steps of a) diluting the fermentation broth 300% (w/w); b) adding 3% (w/w) of CaCl2 (36% (w/w)); and c) adjusting the pH value of the fermentation broth to a pH value of either pH 4.5 or 4.2. The biomass was subsequently removed by centrifugation.

Thus, all known methods require the extensive dilution of the fermentation broth with water prior the removal of the cells in order to achieve good protein yields.

In addition, none of the prior art methods for purifying a protein after fermentation in an industrial scale discloses washing of the particulate matter of the fermentation broth under conditions that favor the solubilization of the protein of interest and/or the desorption of the protein of interest from the particulate matter of the fermentation broth. Instead, all methods described in the art for large-scale protein purification from the fermentation broth require the adjustment of conditions of the fermentation broth that favors the solubilization of the protein of interest and/or the desorption of the protein of interest from the particulate matter in the fermentation broth prior to the removal of the cells from the fermentation broth. This makes the recovery process complicated, work and cost intense and does not allow for a continuous process.

Thus, the prior art techniques for large-scale protein purification are characterized by complicated multi-step procedures that do not allow for a continuous purification process and which result in unsatisfactory yields usually combined with the requirement for extensive dilution of the fermentation broth prior purification of the protein.

Thus, there was a need in the art to facilitate the purification process for a protein of interest obtained by fermentative methods, in particular, to improve the purification process in order to allow for a continuous purification process and to reduce the loss of protein during the purification process due to crystallization and precipitation as well as due to binding of the protein to the particulate matter of the fermentation broth.

BRIEF SUMMARY OF THE INVENTION

The solution to the described problem is provided by the present invention, which is directed to a method of purifying a protein of interest from the particulate matter of a fermentation broth wherein the conditions that promote the solubilization of the protein of interest and/or the desorption of the protein of interest from the biomass are applied in one or more washing steps.

In particular, the present invention is directed to a method of purifying a protein of interest from the particulate matter of a fermentation broth comprising the step of purifying the protein of interest from the particulate matter of the fermentation broth, wherein the step of purifying the protein of interest from the particulate matter of the fermentation broth comprises one or more washing steps, which comprises contacting the particulate matter with a washing solution comprising one or more conditions that favor the solubilization of the protein of interest and/or the desorption of the protein of interest from the particulate matter.

One of the conditions that favor the solubilization of the protein of interest and/or the desorption of the protein of interest from the particulate matter comprises a) a pH value above the pI value of the protein of interest; or b) a pH value below the pI value of the protein of interest and under these conditions a positively charged compound in a concentration leading to a conductivity of 1-100 mS/cm of the washing solution.

DETAILED DESCRIPTION OF THE INVENTION

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art.

It is to be understood that as used in the specification and in the claims, "a" or "an" can mean one or more, depending upon the context in which it is used. Thus, for example, reference to "a cell" can mean that at least one cell can be utilized.

Throughout this application, various publications are referenced. The disclosures of all of these publications and those references cited within those publications in their entireties are hereby incorporated by reference into this application in order to more fully describe the state of the art to which this invention pertains.

The term "purification" or "purifying" refers to a process in which at least one component, e.g., a protein of interest, is separated from at least another component, e.g., a particulate matter of a fermentation broth, and transferred into a different compartment or phase, wherein the different compartments or phases do not necessarily need to be separated by a physical barrier. Examples of such different compartments are two compartments separated by a filtration membrane or cloth, i.e., filtrate and retentate; examples of such different phases are pellet and supernatant or cake and filtrate, respectively.

The term "desorption" refers to a process in which a molecule, e.g., a protein of interest, that is bound, covalent or non-covalent (e.g., by ionic or hydrophobic interactions), to another molecule or substance, e.g., particulate matter of a fermentation broth, is released from said other molecule or substance by breaking or loosening the bond between said molecule and said other molecule or substance. Hence, purification of a protein of interest bound to particulate matter of a fermentation broth requires first desorption of the protein of interest from the particulate matter of the fermentation broth.

The term "washing" is used herein for a process in which a certain volume of washing solution is added to a particulate matter or to a solution comprising particulate matter and the same or similar volume of liquid is subsequently or simultaneously removed from the resulting solution. Therefore, the term "washing" comprises simultaneous addition of a certain volume of washing solution to and removal of the same or similar volume of a liquid from the solution comprising a protein of interest as well as suspending particulate matter in a washing solution and subsequently removing the same or similar volume of a liquid. Therefore, for a fermentation broth comprising particulate matter the term "washing" comprises the replacement of a certain part of the liquid phase of the fermentation broth comprising particulate matter by a washing solution, which is added prior, after or simultaneously to removal of part of the original liquid phase of the fermentation broth comprising particular matter. Due to combined addition of washing solution and the removal of the same or similar volume of original liquid a washing step is not associated with a net increase in working volume with respect to the original volume before the washing step. In this context, a "continuous washing step" is characterized by keeping the working volume during the washing step constant by simultaneous addition and removal of solution at equal quantity. The same understanding shall be applied for the term "contacting particulate matter with a washing solution". Thus, washing of particulate matter of or in a fermentation broth can thus occur simultaneous to or before purification of a protein of interest from the particulate matter of or in a fermentation broth.

In contrast to the term "washing", the term "dilution" describes a process in which a certain volume of a liquid is added to a solution of a compound, e.g., a solution comprising a protein of interest, and thereby increasing the working volume, which leads to a reduction in the concentration of said compound in the solution without subsequent removal of the same or similar volume of liquid from the resulting solution. For instance, the addition of a liquid, e.g., water, to a fermentation broth and subsequent purification of the protein of interest without removal of the same or similar volume of liquid prior to purification of the protein of interest, e.g., but with removal of the combined volume of added liquid and liquid portion of the fermentation broth, is thus considered as a dilution step and not as a washing step.

The term "undiluted fermentation broth" refers to a fermentation broth after conducting the fermentation process prior the addition of substantial amounts of diluent. Thus, the term "undiluted fermentation broth" also encompasses a fermentation broth that has been slightly diluted, e.g., due to the adaptation of certain parameters of the fermentation broth, e.g., dilution due to pH adjustment or conductivity adjustment. In any case, the term "undiluted fermentation broth" does not comprise a fermentation broth that has been diluted more than or equal to 20% (w/w), preferably 10% (w/w).

The term "fermentation in industrial scale" (also called large-scale fermentation) refers to fermentation processes with fermenter volumes of greater than or equal to 20 liters.

The term "pI value" (also abbreviated pH(I) or IEP value) of a molecule as used herein shall refer to the isoelectric point of a molecule, in particular, of an amino acid, peptide or protein, which is the value at which the particular carries no net. As experimental and calculated pI value can slightly differ, herein the term "pI value" refers to the calculated pI value. The pI value can be calculated by using the pK values of individual amino acids as described for example in Bjellqvist et al 1993 or by using a web based interface like web.expasy.org/compute_pi/.

The term "particulate matter" of or in the fermentation broth (also called herein solid matter or solid portion of or in the fermentation broth) shall mean any insoluble matter that is contained in the fermentation broth prior purification of the protein of interest and that can be separated from the rest of the fermentation broth by centrifugation or filtration under conditions known to the skilled person. Examples of particulate matter of or in the fermentation broth are biomass, i.e., dead and/or living cells, insoluble media components, like insoluble components of a complex nitrogen or complex carbon source, salts, flocculants or filter aids.

The term "positively charged compound" shall describe a compound either having under the conditions of the respectively solution comprising the positively charged compound a positive net charge, e.g., a peptide or protein, but also describes a cation within a compound comprising a cation and an anion, e.g., a salt, which compound thus has no net charge, but upon bringing the said compound in solution, anion and cation would dissociate and therewith releasing the positively charged compound.

The term "biomass" shall describe the dead and/or living cells, preferably non-disrupted cells, of the microorganism developed during fermentation.

DETAILED DESCRIPTION

The present invention is directed to a method of purifying a protein of interest from the particulate matter of a fermentation broth comprising the step of purifying the protein of interest from the particulate matter, preferably the biomass, of the fermentation broth, wherein the step of purifying the protein of interest from the particulate matter of the fermentation broth comprises one or more washing steps, which comprises contacting the particulate matter with a washing solution comprising one or more conditions that favor the solubilization of the protein of interest and/or the desorption of the protein of interest from the particulate matter, wherein one of the conditions that favor the solubilization of the protein of interest and/or the desorption of the protein of interest from the particulate matter comprises a) a pH value above the pI value of the protein of interest; or b) a pH value below the pI value of the protein of interest and under these conditions a positively charged compound in a concentration leading to a conductivity of 1-100 mS/cm of the washing solution.

Without being bound to theory, the inventors believe that at a pH close to the pI value of a protein, the protein has no net charge and thus tends to be less soluble. In contrast, at a pH below the pI value of a protein the protein has an overall positive charge and at a pH above the pI value of a protein the protein has an overall negative charge. Both conditions, i.e., a positive as well as a negative net charge reduce the tendency of a protein to aggregate, i.e., positively influence protein recovery. However, as a majority of particulate matter in a fermentation broth, most importantly the cell biomass, has a net negative charge, a protein with a positive net charge is prone to binding to the particulate matter of a fermentation broth and likely to be lost during subsequent separation of the protein. The binding of the protein of interest to the particulate matter can be prevented by addition of a positively charged compound. Surprisingly, the inventors found that applying the conditions positively influencing protein recovery in a washing step during processing of the fermentation broth is superior to applying these conditions to the unprocessed or solely diluted fermentation broth prior to processing of the fermentation broth.

The present invention may be useful for any fermentation in industrial scale, e.g., for any fermentation having culture media of at least 20 liters, preferably, at least 50 liters, more preferably at least 300 liters, further preferred at least 1000 liters. How the actual fermentation has been carried out is relatively inessential for the purification method of present invention. Accordingly, the fermentation time, pH, antifoam or other specific fermentation conditions may be applied according to standard conditions known in the art. Preferably, the fermentation conditions are adjusted to obtain maximum yields of the protein of interest. The fermentation medium may be a minimal medium as described in, e.g., WO 98/37179, or the fermentation medium may be a complex medium comprising complex nitrogen and carbon sources, wherein the complex nitrogen source may be partially hydrolyzed as described in WO 2004/003216. The fermentation may be performed as a batch, a repeated batch, a fed-batch, a repeated fed-batch or a continuous fermentation process. In a fed-batch process, either none or part of the compounds comprising one or more of the structural and/or catalytic elements is added to the medium before the start of the fermentation and either all or the remaining part, respectively, of the compounds comprising one or more of the structural and/or catalytic elements are fed during the fermentation process. The compounds which are selected for feeding can be fed together or separate from each other to the fermentation process. In a repeated fed-batch or a continuous fermentation process, the complete start medium is additionally fed during fermentation. The start medium can be fed together with or separate from the structural element feed(s). In a repeated fed-batch process, part of the fermentation broth comprising the biomass is removed at regular time intervals, whereas in a continuous process, the removal of part of the fermentation broth occurs continuously. The fermentation process is thereby replenished with a portion of fresh medium corresponding to the amount of withdrawn fermentation broth. In a preferred embodiment of the invention, a fed-batch fermentation process is preferred.

Preferably, the particulate matter of or in the fermentation broth comprises at least one component selected from the group consisting of biomass, complex media component, preferably, components of the complex nitrogen and/or complex carbon source, flocculation agent, filter aid, or any solid present in the fermentation broth. Preferably, the particulate matter of or in the fermentation broth comprises biomass, preferably dead and/or living cells, preferably intact cells, preferably non-lysed cells. Preferably, the biomass does not comprise inclusion bodies. Preferably, the particulate matter of or in the fermentation broth comprises biomass and one or more components selected from the group consisting of complex media component, preferably, components of the complex nitrogen and/or complex carbon source, flocculation agent, filter aid, or any solid present in the fermentation broth. Preferably, the particulate matter of or in the fermentation broth is biomass.

The general problem to be solved herein, i.e., to recover a protein of interest where a certain amount of the protein of interest is not in solution is most pronounced when the protein of interest is expressed at relatively high yields. Consequently, a preferred embodiment of the invention is the purification of a protein of interest from the particulate matter of a fermentation broth wherein the protein of interest is expressed in an amount of at least 2 g protein (dry matter)/kg untreated culture medium; preferably in an amount of at least 3 g protein (dry matter)/kg untreated culture medium; more preferably in an amount of at least 5 g protein (dry matter)/kg untreated culture medium, more preferably in an amount of at least 10 g protein (dry matter)/kg untreated culture medium, even more preferably in an amount of at least 20 g protein (dry matter)/kg untreated culture medium.

The method of the invention may be applied to an untreated fermentation broth or to a fermentation broth that has first been subjected to, but not limited to, e.g a temperature adjustment, a pH adjustment, a conductivity adjustment, dilution, and/or addition of flocculants and/or filter aids. Preferably, the purification step described above is applied to an undiluted fermentation broth that has been first been subjected to, but not limited to, e.g, a temperature adjustment, a pH adjustment, or a conductivity adjustment, dilution. More preferably, the purification step described above is applied to an undiluted fermentation broth that has been first been subjected to a pH adjustment and/or a conductivity adjustment and/or temperature adjustment.

Preferably, the temperature of the fermentation broth is between 4-50° C., preferably between 4 and 40° C., prior the beginning of the purification step.

Optionally, the fermentation broth is diluted prior to the beginning of the purification of the protein.

Thus, the present invention is directed to a method of purifying a protein of interest from the particulate matter, preferably the biomass, of a fermentation broth comprising the steps of A) optionally, diluting the fermentation broth comprising the protein of interest before the beginning of the purification of the protein of interest from the particulate matter of the fermentation broth, and B) purifying the protein of interest from the particulate matter of the fermentation broth, wherein the step of purifying the protein of interest from the particulate matter of the fermentation broth comprises one or more washing steps, which comprises contacting the particulate matter with a washing solution comprising one or more conditions that favor the solubilization of the protein of interest and/or the desorption of the protein of interest from the particulate matter, wherein one of the conditions that favor the solubilization of the protein of interest and/or the desorption of the protein of interest from the particulate matter comprises
  a) a pH value above the pI value of the protein of interest; or
  b) a pH value below the pI value of the protein of interest and under these conditions a positively charged compound in a concentration leading to a conductivity of 1-100 mS/cm of the washing solution.

Thereby, the protein of interest is separated from the particulate matter of the fermentation broth.

Thus, the present invention is directed to a method of purifying a protein of interest from the particulate matter, preferably the biomass, of a fermentation broth comprising the steps of A) optionally, diluting the fermentation broth comprising the protein of interest, and B) purifying the protein of interest from the particulate matter of the fermentation broth, wherein the step of purifying the protein of interest from the particulate matter of the fermentation broth comprises aa) one or more washing steps, which comprises contacting the particulate matter with a washing solution comprising one or more conditions that favor the solubilization of the protein of interest and/or the desorption of the protein of interest from the particulate matter, wherein one of the conditions that favor the solubilization of the protein of interest and/or the desorption of the protein of interest from the particulate matter comprises
  a) a pH value above the pI value of the protein of interest; or
  b) a pH value below the pI value of the protein of interest and under these conditions a positively charged compound in a concentration leading to a conductivity of 1-100 mS/cm of the washing solution,
  whereby the protein of interest is solubilized and/or released from the particulate matter into the washing solution, and bb) separating the washing solution comprising the protein of interest from the particulate matter.

In an embodiment of the present invention, the fermentation broth comprising the protein of interest to be purified is diluted up to 5000% (w/w), preferably up to 1000% (w/w), more preferably up to 500% (w/w), preferably between 20-5000% (w/w), preferably between 20-1000% (w/w), preferably between 20-500% (w/w), preferably 10-5000% (w/w), more preferably 10-1000% (w/w), in particular 10-500% (w/w), in particular 20-700% (w/w), in particular 20-500% (w/w) prior to the beginning of the purification of the protein of interest.

Preferably, the step of purifying the protein of interest from the particulate matter, preferably the biomass, of the fermentation broth also comprises one or more washing steps with water, preferably deionized or partially deionized water. Preferably the one or more washing steps with water are applied prior to the one or more washing steps, which comprises contacting the particulate matter with a washing solution comprising one or more conditions that favor the solubilization of the protein of interest and/or the desorption of the protein of interest from the particulate matter. Thus, in a preferred embodiment, the present invention is directed to a method of purifying a protein of interest from the particulate matter of a fermentation broth comprising the steps of A) optionally, diluting the fermentation broth comprising the protein of interest before the beginning of the purification of the protein of interest from the particulate matter of the fermentation broth, and B) purifying the protein of interest from the particulate matter of the fermentation broth, wherein the step of purifying the protein of interest from the particulate matter of the fermentation broth comprises aa) one or more washing steps with water, preferably deionized or partially deionized water and subsequently bb) one or more washing steps, which comprises contacting the particulate matter with a washing solution comprising one or more conditions that favor the solubilization of the protein of interest and/or the desorption of the protein of interest from the particulate matter, wherein one of the conditions that favor the solubilization of the protein of interest and/or the desorption of the protein of interest from the particulate matter comprises
  a) a pH value above the pI value of the protein of interest; or
  b) a pH value below the pI value of the protein of interest and under these conditions a positively charged compound in a concentration leading to a conductivity of 1-100 mS/cm of the washing solution, whereby the protein of interest is solubilized and/or released from the particulate matter into the washing solution, and cc) separating the washing solution comprising the protein of interest from the particulate matter.

Preferably, the one or more washing steps are applied for a time sufficient to allow solubilization of the protein of interest and/or the desorption of the protein of interest from the particulate matter of the fermentation broth. Preferably during the one or more washing steps the particulate matter is contacted with the washing solution for a time period of up to 1 min, up to 5 min, up to 10 min, up to 15 min, up to 30 min, up to 60 min, up to 2 h, up to 3 h, up to 4 h, up to 5 h, up to 10 h, or up to 1 day.

In the present invention, the one or more washing step is a continuous or one or more discontinuous washing step. Preferably, 1-3 washing steps or a continuous washing step is applied. More preferably, the one or more washing steps is a continuous washing step.

Consequently, the method of the present invention allows for the purification of the protein of interest from the particulate matter in a continuous or a discontinuous process. Preferably, the method of purifying a protein of interest from the particulate matter of a fermentation broth is a continuous process, which preferably comprises a continuous washing step with a washing solution comprising one or more conditions that favor the solubilization of the protein of interest and/or the desorption of the protein of interest from the particulate matter. In a preferred embodiment the step of purifying the protein of interest from the particulate matter of the fermentation broth occurs simultaneous to the one or more washing steps. Preferably, the method of the present invention comprises a continuous washing step, wherein the separation of the washing solution comprising the protein of interest from the particulate matter occurs simultaneously to the one or more washing steps. In this embodiment, the step of purifying the protein of interest from the biomass of the fermentation broth occurs simultaneous to the one or more washing steps.

Thus, in a preferred embodiment the present invention refers to a method of purifying a protein of interest from the biomass of a fermentation broth comprising the steps of A) optionally, diluting the fermentation broth comprising the protein of interest, and B) purifying the protein of interest from the biomass of the fermentation broth, wherein the step of purifying the protein of interest from the biomass of the fermentation broth comprises aa) one or more washing steps, which comprises contacting the biomass with a washing solution comprising one or more conditions that favor the solubilization of the protein of interest and/or the desorption of the protein of interest from the biomass, wherein one of the conditions that favor the solubilization of the protein of interest and/or the desorption of the protein of interest from the biomass comprises a) a pH value above the pI value of the protein of interest; or b) a pH value below the pI value of the protein of interest and under these conditions a positively charged compound in a concentration leading to a conductivity of 1-100 mS/cm of the washing solution, whereby the protein of interest is solubilized and/or released from the biomass into the washing solution, and bb) separating the washing solution comprising the protein of interest from the biomass, wherein the one or more washing steps is a continuous washing step, preferably wherein the separation of the washing solution comprising the protein of interest from the particulate matter occurs simultaneously to the one or more washing steps.

In one specific embodiment the liquid portion of the fermentation broth is separated from the solid portion of the fermentation broth prior to the continuous washing step of the particulate matter with a washing solution comprising one or more conditions that favor the solubilization of the protein of interest and/or the desorption of the protein of interest from the particulate matter. In another specific embodiment the liquid portion of the fermentation broth is separated from the solid portion of the fermentation broth simultaneous to the one or more washing steps.

Preferably, the step of purifying the protein of interest from the particulate matter of the fermentation broth comprising liquid and solid portion comprises a diafiltration step, wherein the diafiltration step comprises one or more of said washing steps with a washing solution comprising one or more conditions that favor the solubilization of the protein of interest and/or the desorption of the protein of interest from the particulate matter as described herein. The use of these continuous or partially continuous processes reduces the need for large storage vessels in comparison to a discontinuous process.

In a preferred embodiment, the step of purifying the protein of interest from the particulate matter of the fermentation broth does not comprise a centrifugation step, preferably, does not comprise a non-continuous centrifugation step.

Alternatively, the step of purifying the protein of interest from the particulate matter comprises a step of separating the particulate matter from the fermentation broth, e.g., by centrifugation, and subsequently one or more washing steps of the particulate matter separated from the fermentation broth. Thus, in a preferred embodiment the method of purifying a protein of interest from the particulate matter, preferably the biomass, of a fermentation broth comprises the steps of A) optionally, diluting the fermentation broth comprising the protein of interest, B) separating the particulate matter from the fermentation broth resulting in a solid portion of the fermentation broth comprising the particulate matter and a liquid portion of the fermentation broth, and C) applying one or more washing steps to the solid portion of the fermentation broth comprising contacting the solid portion of the fermentation broth comprising the particulate matter with a washing solution comprising one or more conditions that favor the solubilization of the protein of interest and/or the desorption of the protein of interest from the particulate matter, wherein one of the conditions that favor the solubilization of the protein of interest and/or the desorption of the protein of interest from the particulate matter comprises a) a pH value above the pI value of the protein of interest; or b) a pH value below the pI value of the protein of interest and under these conditions a positively charged compound in a concentration leading to a conductivity of 1-100 mS/cm of the washing solution.

In this particular embodiment, the liquid portion of the fermentation broth after removal of the particulate matter is preferably combined with the one or more washing solutions recovered after washing therewith the solid portion of the fermentation broth.

The fermentation broth comprising the protein of interest does not need to be diluted prior the purification step. The omission of the dilution step saves time and resources and reduces number and volume of storage vessels. Beyond, it reduces the amount of water which has to be disposed.

Thus, in a preferred embodiment, the protein of interest is purified from the particulate matter of the undiluted fermentation broth. Preferably, prior purification there is merely a dilution of the fermentation broth of less than less than 20%, less than 10%, less than 5%, less than 2% (w/w), or no dilution at all.

Hence, preferably, the present invention is directed to a method of purifying a protein of interest from the particulate matter, preferably the biomass, of a fermentation broth comprising the step of purifying the protein of interest from the particulate matter of the undiluted fermentation broth, wherein the step of purifying the protein of interest from the particulate matter of the undiluted fermentation broth comprises simultaneous to the purification of the protein of interest from the particulate matter of the fermentation broth one or more washing steps, which comprises contacting the particulate matter with a washing solution comprising one or more conditions that favor the solubilization of the protein of interest and/or the desorption of the protein of interest from the particulate matter, wherein one of the conditions that favor the solubilization of the protein of interest and/or the desorption of the protein of interest from the particulate matter comprises a) a pH value above the pI value of the protein of interest; or b) a pH value below the pI value of the protein of interest and under these conditions a positively charged compound in a concentration leading to a conductivity of 1-100 mS/cm of the washing solution.

In a preferred embodiment, the concentration of particulate matter of the fermentation broth is increased prior to purifying the protein of interest from the particulate matter of the fermentation broth, preferably, prior to the one or more washing steps, preferably by concentration, preferably by means of incomplete filtration or by centrifugation in combination with partial removal of the centrifugation centrate.

Preferably, an adjustment of the pH value of the fermentation broth is performed before the beginning of the purification of the protein of interest from the particulate matter of the fermentation broth. Preferably, the pH value of the fermentation broth is adjusted before the purification of the protein of interest from the particulate matter of the fermentation broth to pH 7.5 to pH 12.5, preferably to pH 8.5 to pH 12.0, preferably pH 8.5 to 10.0 or to pH 4.5 to pH 9.5, preferably, pH 4.5 to pH 9.0, preferably pH 5.0 to pH 8.5, preferably 5.5 to 8.0.

It is within the skilled person's general knowledge to optimize the specific pH level in relation to the specific characteristics of the protein of interest to be recovered.

Preferably, the pH value of the fermentation broth is adjusted before the purification of the protein of interest from the particulate matter of the fermentation broth to a pH of preferably between 0.2-0.75, between 0.2-1.0, between 0.2-2.0, between 0.2-3.0, between 0.2-4.0, between 0.5-1.0, between 0.5-2.0, between 0.5-3.0, or between 0.5-4.0 pH value units above or below the pI value of the protein of interest, or preferably at least 0.2, at least 0.5, at least 0.75, at least 1.0, at least 1.25, at least 1.5, at least 1.75, at least 2.5, at least 2.75, at least 3.0, at least 3.25, at least 3.5, at least 3.75, or at least 4.0 pH value units above or below the pI value of the protein of interest.

In a preferred embodiment, the pI value of the protein of interest is between pH 5.5 and pH 10.0, preferably between pH 5.5 and 7.5, preferably between pH 7.0 and pH 10.0, or preferably between pH 8.0 and pH 9.5.

Preferably, before the beginning of the purification of the protein of interest from the particulate matter of the fermentation broth the conductivity of the fermentation broth is adjusted to a conductivity of 1-100 mS/cm, preferably, 1-50 mS/cm, more preferably, 10 mS/cm to 50 mS/cm; even more preferably 1-25 mS/cm of the fermentation broth by adding an under these conditions positively charged compound before the purification of the protein of interest from the particulate matter of the fermentation broth.

The conductivity of the fermentation broth (after the addition of the positive charged component and optionally the pH adjustment) is preferably in the range of from 1 mS/cm to 100 mS/cm; more preferably in the range of from 1 mS/cm to 50 mS/cm; more preferably in the range of from 10 mS/cm to 50 mS/cm; even more preferably in the range of from 1 mS/cm to 25 mS/cm. The conductivity maybe monitored, e.g., with a conductivity meter.

In a preferred embodiment one of the conditions of the washing solution applied during the purification step that favor the solubilization of the protein of interest and/or the desorption of the protein of interest from the particulate matter comprises a pH value of the washing solution above the pI value of the protein of interest and the pH value of the washing solution is at least 0.2 pH value units above the pI value of the protein of interest. In this embodiment, preferably, the pH of the washing solution is adjusted to a pH of preferably between 0.2-0.75, between 0.2-1.0, between 0.2-2.0, between 0.2-3.0, between 0.2-4.0, between 0.5-1.0, between 0.5-2.0, between 0.5-3.0, or between 0.5-4.0 pH value units above the pI value of the protein of interest, or at least 0.5, at least 0.75, at least 1.0, at least 1.25, at least 1.5, at least 1.75, at least 2.5, at least 2.0, at least 2.75, at least 3.0, at least 3.25, at least 3.5, at least 3.75, or at least 4.0 pH value units above the pI value of the protein of interest. Preferably, the pH of the washing solution has a pH value of pH 8.5 to pH 12.5, preferably, pH 8.5 to pH 10.0. Preferably, the pH of the washing solution has a pH value of pH 5.0 to pH 10 and preferably, the protein of interest is a protease or amylase. Preferably, the pH of the washing solution has a pH value of pH 8.5 to pH 12.5, preferably, pH 8.5 to pH 10.0 and the pI value of the protein of interest is at a pH value of pH 5.5 to pH 8.4, preferably the protein of interest is a protease, preferably a serine protease, or an amylase.

Preferably, the pH of the washing solution has a pH value of pH 8.5 to pH 12.5, preferably, pH 8.5 to pH 10.0 and the protein of interest is a protease, preferably a serine protease, preferably the protease having pI value between pH 5.5 to pH 8.4.

Preferably, the pH of the washing solution has a pH value of pH 5.5 to pH 12.0, preferably, pH 6.0 to pH 12.0, preferably pH 6.0 to pH 11.0 and the pI value of the protein of interest is at a pH value of pH 5.0 to pH 7.0, preferably below pH 7.0 and the protein of interest is an amylase.

In a preferred embodiment, the pH of the washing solution has a pH value of pH 8.5 to pH 13.0, preferably, pH 8.5 to pH 12.0, more preferably 8.5 to 10.0 and the one or more washing steps are performed at a temperature of 4° C. to 50° C., preferably of 4° C. to 40° C.

Preferably the washing solution is an aqueous solution having the properties as described herein.

In a preferred embodiment one of the conditions of the washing solution applied during the purification step that favor the solubilization of the protein of interest and/or the desorption of the protein of interest from the particulate matter comprises a pH value of the washing solution below the pI value of the protein of interest and under these conditions a positively charged compound in a concentration leading to a conductivity of 1-100 mS/cm, preferably, 1-50 mS/cm, more preferably 10-50 mS/cm, even more preferably 1-25 mS/cm of the washing solution and the pH value of the washing solution is at least 0.2 pH value units below the pI value of the protein of interest.

In this embodiment, preferably, the pH of the washing solution is adjusted to a pH of preferably between 0.2-0.75, between 0.2-1.0, between 0.2-2.0, between 0.2-3.0, between 0.2-4.0, between 0.5-1.0, between 0.5-2.0, between 0.5-3.0, or between 0.5-4.0 pH value units below the pI value of the protein of interest, or is at least 0.2, at least 0.5, at least 0.75, at least 1.0, at least 1.25, at least 1.5, at least 1.75, at least 2.0, at least 2.5, at least 2.75, at least 3.0, at least 3.25, at least 3.5, at least 3.75, or at least 4.0 pH value units below the pI value of the protein of interest. In this embodiment, preferably, the conductivity of the washing solution (after the addition of a positive charged component and the pH adjustment) is preferably in the range of from 1 mS/cm to 100 mS/cm; more preferably in the range of from 1 mS/cm to 50 mS/cm; even more preferably in the range of from 1 mS/cm to 25 mS/cm.

Preferably, the pH of the washing solution has a pH value of pH 4.0 to 9.5, preferably pH 4.5 to pH 8.0, preferably, pH 4.5 to pH 7.5, preferably, pH 4.5 to 6.0, preferably pH 4.5 to pH 5.5, preferably 5.0 to 5.5.

Preferably, the pH of the washing solution has a pH value of pH 5.0 to pH 8.0, preferably, pH 5.5 to pH 8.0. This embodiment allows in particular for serine-protease to work in pH range which stabilizes the protease and reduces the proteolytic activity of the protease.

Preferably, the pH of the washing solution has a pH value of pH 4.0 to pH 5.5, preferably, pH 4.5 to pH 5.0. This embodiment allows in particular the purification of amylases.

Preferably, in this embodiment the pH of the washing solution has a pH value of pH 4.0 to pH 8.0, preferably, pH 5.5 to pH 8.0, preferably, the pH of the washing solution is at least 0.2, at least 0.5, at least 0.75, at least 1.0, at least 1.25, at least 1.5, at least 1.75, at least 2.0, at least 2.5 below the pI of the protein, and the conductivity of the washing solution (after the addition of the positively charged component and the pH adjustment) is preferably in the range of from 1 mS/cm to 100 mS/cm, further preferred in the range of 1 mS/cm to 50 mS/cm, more preferably in the range of from 1 mS/cm to 25 mS/cm and the pI value of the protein of interest is at a pH value of pH 5.5 to pH 12, preferably pH 5.5 to pH 7.5, preferably, pH 8.2 to pH 12, preferably pH 6.5 to pH 8.4, preferably the protein of interest is a protease, preferably a serine protease, or an amylase.

Preferably, in this embodiment the pH of the washing solution has a pH value of pH 5.0 to pH 8.0 and the conductivity of the washing solution (after the addition of the positively charged component and the pH adjustment) is preferably in the range of from 1 mS/cm to 100 mS/cm, further preferred in the range of 1 mS/cm to 50 mS/cm, more preferably in the range of from 1 mS/cm to 25 mS/cm and the protein of interest is a protease, preferably a serine protease, preferably the protease having pI value between pH 8.2 to pH 12.0.

Preferably, the pH of the washing solution has a pH value of pH 4.0 to pH 7.0, preferably, pH 4.0 to pH 5.5 and the conductivity of the washing solution (after the addition of the positively charged component and the pH adjustment) is preferably in the range of from 1 mS/cm to 100 mS/cm, further preferred in the range of 1 mS/cm to 50 mS/cm, more preferably in the range of from 1 mS/cm to 25 mS/cm and the pI value of the protein of interest is at a pH value of pH 5.5 to pH 7.5, and the protein of interest is an amylase.

In a preferred embodiment, the present invention is directed to a method of purifying a protein of interest from the particulate matter, preferably the biomass, of a fermentation broth comprising the steps of A) optionally, diluting the fermentation broth comprising the protein of interest, and B) purifying the protein of interest from the particulate matter of the fermentation broth, wherein the step of purifying the protein of interest from the particulate matter of the fermentation broth comprises simultaneous to the purification of the protein of interest from the particulate matter of the fermentation broth one or more washing steps, which comprises contacting the particulate matter with a washing solution comprising one or more conditions that favor the solubilization of the protein of interest and/or the desorption of the protein of interest from the particulate matter, wherein one of the conditions that favor the solubilization of the protein of interest and/or the desorption of the protein of interest from the particulate matter comprises a pH value above the pI value of the protein of interest, wherein the condition that favors the solubilization of the protein of interest and/or the desorption of the protein of interest comprises a pH value of pH 7.5 to pH 13.0, preferably pH 8.0 to pH 12.0, more preferably pH 8.5 to pH 10.0, preferably wherein the protein of interest is a protease, preferably, a serine protease, or an amylase.

In a preferred embodiment, the present invention is directed to a method of purifying a protein of interest from the particulate matter, preferably the biomass, of a fermentation broth comprising the steps of A) optionally, diluting the fermentation broth comprising the protein of interest, and B) purifying the protein of interest from the particulate matter of the fermentation broth, wherein the step of purifying the protein of interest from the particulate matter of the fermentation broth comprises simultaneous to the purification of the protein of interest from the particulate matter of the fermentation broth one or more washing steps, which comprises contacting the particulate matter with a washing solution comprising one or more conditions that favor the solubilization of the protein of interest and/or the desorption of the protein of interest from the particulate matter, wherein one of the conditions that favor the solubilization of the protein of interest and/or the desorption of the protein of interest from the particulate matter comprises a pH value below the pI value of the protein of interest and under these conditions a positively charged compound in a concentration leading to a conductivity of 1-100 mS/cm of the washing solution, wherein the condition of the washing solution that favors the solubilization of the protein of interest and/or the desorption of the protein of interest comprises a pH value of pH 4.0 to pH 9.5, preferably, pH 4.5 to pH 9.0, more preferably, pH 5.0 to pH 8.5 and under these conditions a positively charged compound in a concentration leading to a conductivity of 1-100 mS/cm of the washing solution, preferably wherein the protein of interest is a protease, preferably, a serine protease, or an amylase.

Preferably, the positively charged compound mentioned above is a cation of a salt, preferably, wherein the cation of the salt is a monovalent or divalent cation, preferably, a sodium, a calcium, or a magnesium cation, or wherein the positively charged compound is an amino acid, a peptide or a protein with a pI value above the pI value of the protein of interest, or a combination thereof.

Suitable cations of a salt are cations of Li, Na, K, Mg, Ca, Al, Fe, or NH4 cations, or combinations thereof. Preferred cations of a salt are sodium, calcium, ammonia or magnesium cations or combinations thereof. Preferred anions of the salt comprising the cation are phosphate, sulphate, nitrate, acetate, and/or chloride, formiate, carbonate. A preferred embodiment NaCl, Na2SO4, CaCl2 or MgCl2 NH4SO4, NaAcetate, NaFormiate or combinations thereof are used for the addition of a positively charged compound.

In a preferred embodiment, the purification of the protein of interest from the particulate matter is achieved by filtration, preferably by microfiltration, or by centrifugation, preferably, by decanter centrifugation or disc stack centrifugation.

In a preferred embodiment, the purification of the protein of interest from the particulate matter is achieved by continuous filtration or continuous centrifugation.

Preferably, the purification of the protein of interest from the particulate matter is achieved by a method selected from the group consisting of cross-flow filtration, preferably, with tubular modules, with plate modules, or with hollow fibers, or dead-end filtration, preferably, drum filtration, disc filter, belt filter, or filter press.

In another preferred embodiment, the washing solution comprises at least one solution selected from the group consisting of a buffer solution, a salt solution, a microfiltration filtrate, an ultrafiltration filtrate, centrifugation centrate, water, and any other process stream. The use of downstream process streams saves resources as already existing streams are recycled. Moreover, the use of downstream process streams as a washing solution increases the yield of the protein of interest as usually residual amounts of protein are contained in these process streams, which are then recovered.

In a preferred embodiment, the washing solution is a buffer solution. Suitable buffer solutions are phosphate buffers, carbonate buffers, acetate buffers or formiate buffers.

Preferably, the fermentation broth is obtained from the fermentation of a microorganism expressing the protein of interest, preferably, the microorganism is a prokaryote or a eukaryote.

Preferably, the microorganism is a bacteria, an archaea, a fungal cell, a yeast cell or a eukaryotic cell.

Useful prokaryotes are bacterial cells such as gram positive or gram negative bacteria. Preferred useful gram positive bacteria include, but are not limited to, a *Bacillus* cell, e.g., *Bacillus alkalophius, Bacillus amyloliquefaciens, Bacillus brevis, Bacillus circulans, Bacillus clausii, Bacillus coagulans, Bacillus firmus, Bacillus Jautus, Bacillus lentus, Bacillus licheniformis, Bacillus megaterium, Bacillus pumilus, Bacillus stearothermophilus, Bacillus subtilis,* and *Bacillus thuringiensis.* Most preferred, the prokaryote is a *Bacillus* cell, preferably, a *Bacillus* cell of *Bacillus subtilis, Bacillus pumilus, Bacillus licheniformis,* or *Bacillus lentus.*

Some other preferred bacteria include strains of the order Actinomycetales, preferably, *Streptomyces,* preferably *Streptomyces spheroides* (ATTC 23965), *Streptomyces thermoviolaceus* (IFO 12382), *Streptomyces lividans* or *Strep-*

*tomyces murinus* or *Streptoverticillum verticillium* ssp. *verticillium.* Other preferred bacteria include *Rhodobacter sphaeroides, Rhodomonas palustri, Streptococcus lactis.* Further preferred bacteria include strains belonging to *Myxococcus,* e.g., *M. virescens.*

Preferred gram negative bacteria are *Escherichia coli* and *Pseudomonas* sp., preferably, *Pseudomonas purrocinia* (ATCC 15958) or *Pseudomonas fluorescens* (NRRL B-11).

The microorganism may be a fungal cell. "Fungi" as used herein includes the phyla Ascomycota, Basidiomycota, Chytridiomycota, and Zygomycota as weil as the Oomycota and Deuteromycotina and all mitosporic fungi. Representative groups of Ascomycota include, e.g., *Neurospora, Eupenicillium* (=*Penicillium*), *Emericella* (=*Aspergillus*), *Eurotium* (=*Aspergillus*), *Myceliophthora,* C1, and the true yeasts listed below. Examples of Basidiomycota include mushrooms, rusts, and smuts. Representative groups of Chytridiomycota include, e.g., *Allomyces, Blastocladiella, Coelomomyces,* and aquatic fungi. Representative groups of Oomycota include, e.g. Saprolegniomycetous aquatic fungi (water molds) such as *Achlya.* Examples of mitosporic fungi include *Aspergillus, Penicillium, Candida,* and *Alternaria.* Representative groups of Zygomycota include, e.g., *Rhizopus* and *Mucor.*

Some preferred fungi include strains belonging to the subdivision Deuteromycotina, class Hyphomycetes, e.g., *Fusarium, Humicola, Tricoderma, Myrothecium, Verticillum, Arthromyces, Caldariomyces, Ulocladium, Embellisia, Cladosporium* or *Dreschlera,* in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes.*

Other preferred fungi include strains belonging to the subdivision Basidiomycotina, class Basidiomycetes, e.g. *Coprinus, Phanerochaete, Coriolus* or *Trametes,* in particular *Coprinus cinereus* f. *microsporus* (IFO 8371), *Coprinus macrorhizus, Phanerochaete chrysosporium* (e.g. NA-12) or *Trametes* (previously called *Polyporus*), e.g. *T. versicolor* (e.g. PR4 28-A).

Further preferred fungi include strains belonging to the subdivision Zygomycotina, class Mycoraceae, e.g. *Rhizopus* or *Mucor,* in particular *Mucor hiemalis.*

The fungal hast cell may be a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus *Schizosaccharomyces*), Nadsonioideae, Lipomycoideae, and Saccharomycoideae (e.g. genera *Kluyveromyces, Pichia,* and *Saccharomyces*). The basidiosporogenous yeasts include the genera *Leucosporidim, Rhodosporidium, Sporidiobolus, Filobasidium,* and *Filobasidiella.* Yeasts belonging to the Fungi Imperfecti are divided into two families, Sporobolomycetaceae (e.g., genera *Sporobolomyces* and *Bullera*) and Cryptococcaceae (e.g. genus *Candida*). In another embodiment, the fungal host cell is a filamentous fungal cell.

The host cell may also be a eukaryote, such as a mammalian cell, an insect cell, or a plant cell.

The method of the invention can be applied for recovering any protein of interest.

Preferably, the protein of interest is an enzyme, in particular an enzyme classified as a oxidoreductase (EC 1), a transferase (EC 2), a hydrolase (EC 3), a lyase (EC 4), a Isomerase (EC 5), or a Ligase (EC 6) (EC-numbering according to Enzyme Nomenclature, Recommendations (1992) of the Nomenclature Committee of the International Union of Biochemistry and Molecular Biology including its supplements published 1993-1999).

Most preferably, the enzyme is a hydrolase (EC 3), preferably, a glycosidase (EC 3.2) or a peptidase (EC 3.4). Especially preferred enzymes are enzymes selected from the group consisting of an amylase (in particular an alpha-amylase (EC 3.2.1.1)), a cellulase (EC 3.2.1.4), a lactase (EC 3.2.1.108), a mannanase (EC 3.2.1.25), a lipase, a phytase (EC 3.1.3.8), and a protease; in particular an enzyme selected from the group consisting of amylase, protease, lipase, mannanase, phytase, and cellulase, preferably, amylase or protease, preferably, a serine protease (EC 3.4.21). Most preferred is a serine protease. In a preferred embodiment, the protein of interest is a detergent enzyme.

In a particular preferred embodiment the following hydrolases are preferred:

Proteases: Suitable proteases include those of bacterial or fungal origin. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Preferably, the subtilisin protease is a serine protease that uses a catalytic triad composed of Asp32, His64 and Ser221 (subtilisin BPN' numbering), preferably, the pI value of the subtilisin protease is between pH 7.0 and pH 10.0, preferably between pH 8.0 and pH 9.5. Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Additional useful proteases are described in WO2012080201 and WO2013060621.

A further preferred protease is a protease according to SEQ ID NO: 1 of DE10201221 5642A1 and variants thereof, wherein the preferred variants comprises one or more mutations at position 3, 4, 99, 194 and 199 (using the numbering of the alkaine protease from DSM5483), preferably comprising one or more of the following mutations: S3T, V4I, R99E, V194M, and V199I, preferably, S3T, V4I, R99E, and V199I, more preferably R99E, or R99E in combination with two additional mutations selected from the group consisting of S3T, V4I, and V199I, preferably SEQ ID NO: 1 of DE102012215642A1 with R99E, or S3T, V4I, V194M, and V199I, or S3T, V4 I and V199I. A further preferred protease is a protease according to SEQ ID NO: 2 of DE102012215642A1 and variants thereof, wherein the preferred variants comprises a mutation at position 99 and an insertion between position 99 and 100, wherein the insertion is an aspartate (Asp, D) residue. In this embodiment preferably the mutation at position 99 is S99A. Further preferred protease variants are SEQ ID NO: 7 of DE102011118032A1 comprising the mutations S3T, V4 I and V205I or SEQ ID NO:8 of DE102011118032A1 comprising the mutations S3T, V4I, V193M, V199I, and L211D using the numbering of the alkaine protease from DSM5483.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Examples of useful lipases include lipases from Humicola (synonym Thermomyces), e.g. from H. lanuginosa (T. lanuginosus), as described in EP 258 068 and EP 305 216 or from H. insolens as described in WO 96/13580, a Pseudomonas lipase, e.g. from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g. from B. subtilis (Dartois et al. (1993), Biochemica et Biophysica Acta, 1131, 253-360), B. stearothermophilus (JP 64/744992) or B. pumilus (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases: Suitable amylases (alpha and/or beta) include those of bacterial or fungal origin. Chemically modified or protein engineered mutants are included. Amylases include, for example, alpha-amylases obtained from Bacillus, e.g. a special strain of B. licheniformis, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BANT™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Oxidoreductases: Oxidoreductases that may be treated according to the invention include peroxidases, and oxidases such as laccases.

Peroxidases: An enzyme exhibiting peroxidase activity may be any peroxidase enzyme comprised by the enzyme classification (EC 1.11.1.7), or any fragment derived therefrom, exhibiting peroxidase activity.

Particularly, a recombinantly produced peroxidase is preferred, e.g., a peroxidase derived from a *Coprinus* sp., in particular *C. macrorhizus* or *C. cinereus* according to WO 92/16634, or a variant thereof, e.g., a variant as described in WO 93/24618 and WO 95/10602.

Laccases and Laccase related enzymes: In the context of this invention, laccases and laccase related enzymes contemplate any laccase enzyme comprised by the enzyme classification (EC 1.10.3.2), any chatechol oxidase enzyme comprised by the enzyme classification (EC 1.10.3.1), any bilirubin oxidase enzyme comprised by the enzyme classification (EC 1.3.3.5) or any monophenol monooxygenase enzyme comprised by the enzyme classification (EC 1.14.18.1).

The microbial laccase enzyme may be derived from bacteria or fungi (including filamentous fungi and yeasts) and suitable examples include a laccase derivable from a strain of *Aspergillus, Neurospora*, e.g., *N. crassa, Podospora, Botrytis, Collybia*, Fomes, Lentinus, *Pleurotus, Trametes*, e.g., *T. villosa* and *T. versicolor, Rhizoctonia*, e.g., *R. solani, Coprinus*, e.g. *C. plicatilis* and *C. cinereus, Psatyrella, Myceliophthora*, e.g. *M. thermophila, Schytalidium, Polyporus*, e.g., *P. pinsitus, Phlebia*, e.g., *P. radita* (WO 92/01046), or *Coriolus*, e.g., *C. hirsutus* (JP 2-238885), in particular laccases obtainable from *Trametes, Myceliophthora, Schytalidium* or *Polyporus*.

Further, protein engineered variants of a protein of interest, made by recombinant DNA techniques or by chemical modification, may be of particular interest.

The purified protease resulting from the method of the present invention may be further processed by methods known in the art. For example, the protease may be recovered by conventional procedures including, but not limited to, further filtration, e.g., ultra-filtration and microfiltration, extraction, decolorization, chromatography, de-odorization, spray-drying, evaporation, precipitation or crystallization and centrifugation.

The method of purifying a protein of interest from the particulate matter of a fermentation broth of the present invention can be used for the preparation of a liquid protein formulation. Preferably, the liquid protein formulation is a protein concentrate, preferably a stabilized enzyme formulation comprising one or more enzyme stabilizer. In another embodiment the liquid protein formulation is a detergent formulation. Thus, the method of the present invention can be used to prepare a detergent formulation. In a preferred embodiment, the protein of interest is a detergent enzyme and the liquid protein formulation is a detergent formulation comprising the detergent enzyme, one or more detergent, one or more enzyme stabilizer and optionally, one or more other detergent enzymes.

The invention is further illustrated in the following examples which are not intended to be in any way limiting to the scope of the invention as claimed.

EXAMPLES

The following examples only serve to illustrate the invention. The numerous possible variations that are obvious to a person skilled in the art also fall within the scope of the invention.

Unless otherwise stated the following experiments have been performed by applying standard equipment, methods, chemicals, and biochemicals as used in genetic engineering and fermentative production of chemical compounds by cultivation of microorganisms. See also Sambrook et al. (Molecular Cloning: A Laboratory Manual. 2nd edition, Cold Spring Harbor Laboratory, Cold Spring Harbor Laboratory Press, Cold Spring Harbor, N Y, 1989) and Chmiel et al. (Bioprocesstechnik 1. Einfuhrung in die Bioverfahrenstechnik, Gustav Fischer Verlag, Stuttgart, 1991).

Example 1

Washing with a pH Below the pI Value

A protease containing fermentation broth was obtained by culturing *Bacillus licheniformis* producing a alkaline protease enzyme derived *Bacillus lentus* DSM 5483 as described for example in SEQ ID NO: 1 of DE102012215642A1 comprising the mutation R99E using the numbering of the alkaine protease from DSM5483.

The protease was purified by diafiltration of the undiluted fermentation broth without prior removal of the biomass by centrifugation or other means using a microfiltration membrane with a tubular module with one channel and four volumes of diafiltration washing solution at a transmembrane pressure of 1.3 bar. The diafiltration washing solution was buffered with 10 mM sodium acetate (NaOAc) for pH=6, ammonium acetate (NH4OAc) for pH=7.5, respectively, the pH was adjusted to either pH6 or pH7.5, and conductivity of the washing solution was adjusted with Na2SO4 to 15 mS/cm. The protease activity of the different fermentation brothes was in the range of 5% CV (coefficient of variation or relative standard variation).

TABLE 1

| Trial number | Conductivity* [mS/cm] | Mass broth [g] | T [° C.] | pH of diafiltration solution [—] | Loss over MF-Retentate [%] |
|---|---|---|---|---|---|
| 1 | 18.06 | 5800 | 25 | 7.5 | 6.0 |
| 2 | 18.06 | 5800 | 25 | 7.5 | 6.4 |
| 3 | 20.5 | 3273 | 25 | 6 | 5.8 |
| 4 | 20.4 | 3273 | 35 | 6 | 4.7 |
| 5 | 19.06 | 2500 | 35 | 6 | 4.5 |
| 6 | 20.3 | 2500 | 35 | 6 | 5.5 |
| 7 | 18.21 | 2775 | 35 | 6 | 4.8 |

*of the fermentation broth

From the data shown in Table 1 it can be derived that when using during microfiltration a diafiltration washing solution with a pH below the pI of the protease (pI=pH 8.3), i.e., pH 7.5, in combination with a positively charged compound, e.g., Na2SO4, with a conductivity of 15 mS/cm, the loss of protease over the microfiltration retentate is in average 6.2%. When the pH of the diafiltration washing solution is further decreased to pH 6.0 the loss of protease over the microfiltration retentate is further decreased to in average 5%.

Thus, the data in Table 1 demonstrates that decreasing the pH of the diafiltration washing solution below the pI of the protein of interest (pI here pH 8.3) reduces the loss of protease in the microfiltration step (i.e., the yield of the protein of interest in the purification process increases) when a positively charged compound (in this case Na2SO4 up to a conductivity of 15 mS/cm) is included in the diafiltration washing solution.

Example 2

Washing with a pH Above the pI Value

In this example, the same setting has been used as in example 1, except that a pH above the pI value of the protease has been adjusted in the diafiltration washing solution and no additional positively charged compound has been added (washing solution solely buffered with 10 mM NaHCO₃). The protease activity of the different fermentation brothes lay in the range of 2% CV (coefficient of variation or relative standard variation).

TABLE 2

| Trial number | Conductivity* [mS/cm] | Mass broth [g] | T [° C.] | pH Diafiltration [—] | Loss over MF-Retentate [%] |
|---|---|---|---|---|---|
| 1 | 21.6 | 3273 | 25 | 9 | 4.2 |
| 2 | 22.7 | 3273 | 10 | 9 | 4.6 |
| 3 | 20.60 | 6546 | 25 | 9 | 4.9 |
| 4 | 17.6 | 3273 | 25 | 9 | 3.6 |
| 5 | 17.31 | 3273 | 35 | 9 | 4.2 |
| 6 | 19.17 | 6546 | 25 | 8.5 | 6.0 |

*of the fermentation broth

From the data shown in Table 2 it can be derived that when using during microfiltration a diafiltration washing solution with a pH above the pI of the protease (pH 8.3), i.e., pH 8.5, the loss of protease over the microfiltration retentate is 6.0%. When the pH is further increased to pH 9 the loss of protease over the microfiltration retentate further decreases to in average 4.3%.

Thus, the data in Table 2 demonstrates that increasing the pH of the diafiltration washing solution above the pI of the protease (pH 8.3) reduces the loss of protein of interest in the microfiltration step. The addition of a positively charged compound is not necessary.

Example 3

Effect of Washing Compared to Simple Dilution

A protease containing fermentation broth was obtained by culturing *Bacillus licheniformis* producing a subtilisin protease as described above.

The protease was purified by microfiltration of the fermentation broth. The fermentation broth was either diluted with washing solution (buffered with 10 mM NaOAc, pH6, conductivity adjusted with Na2SO4 to 15 mS/cm) prior microfiltration or washed during microfiltration with the same amount of the same kind of washing solution. The protease activity of the different fermentation brothes lay in the range of 3.6% CV (Table 3) and 1.1% CV (Table 4).

TABLE 3

| Trial number | Conductivity* [mS/cm] | Mass broth [g] | Mass predilution soution [g] | Mass diafiltration solution [g] | Dilution [%] | MK | MA | Loss over MF-Retentate [%] |
|---|---|---|---|---|---|---|---|---|
| 1 | 17.48 | 5000 | 110 | 9855 | 2.2 | 1 | 2.03 | 24.7 |
| 2 | 18.53 | 4000 | 7917 | 0 | 113 | 3.06 | 0 | 39.2 |

MK = 1: no concentration

MA = 0: no diafiltration

*of the fermentation broth

TABLE 4

| Trial number | Conductivity* [mS/cm] | Mass broth [g] | Mass predilution soution [g] | Mass diafiltration solution [g] | Dilution [%] | MK | MA | Loss over MF-Retentate [%] |
|---|---|---|---|---|---|---|---|---|
| 1 | 18.1 | 2000 | 44.8 | 7848 | 2.2 | 1.05 | 4.18 | 4.2 |
| 2 | 18.09 | 2000 | 8000 | 0 | 400 | 4.93 | 0 | 28.0 |

MK = 1: no concentration

MA = 0: no diafiltration

*of the fermentation broth

From the data shown in Table 3 and 4 it can be derived that when performing a washing step with a washing solution that favors the solubilization of the protease and/or the desorption of the protease from the particulate matter instead of a simple dilution step with the same type of solution, the loss of protease during microfiltration is reduced from 39.2% to 24.7% (Table 3) and from 28% to 4.2% (Table 4), respectively.

Thus, the data in Table 3 and 4 demonstrates that a washing step with a solution that favors the solubilization of the protein of interest and/or the desorption of the protein from the particulate matter is superior to solely diluting the fermentation broth with a diluent having the same properties as the washing solution.

Example 4

Washing with and without Desorbing Conditions

A protease containing fermentation broth was obtained as described in example 1.

The protease was purified by diafiltration of the undiluted fermentation broth without prior removal of the biomass by centrifugation using a tubular microfiltration membrane with one channel and 3 mm inner diameter. The washing during the microfiltration was either done with water (pH 7.5) or with a diafiltration washing solution buffered with 10 mM $NaHCO_3$ at pH 7.5 with 100 mM NaCl. The protease activity of the different fermentation brothes was in the range of 10% CV

TABLE 5

| Trial number | Conductivity* [mS/cm] | Mass broth [g] | T [°C.] | Diafiltration solution | Retention [%] | Loss over MF-Retentate [%] |
|---|---|---|---|---|---|---|
| 1 | 16.1 | 1400 | 35 | water | 42 | 8 |
| 2 | 16.5 | 1400 | 35 | NaCl | 17 | 3 |

*of the fermentation broth

From the data shown in Table 5 it can be derived that washing during the microfiltration step with water leads to a loss of protease over the microfiltration retentate of 8%. The use of a saline solution leads to a reduced loss of protease over the microfiltration retentate of 3%.

Thus, the data in Table 5 demonstrates that when using during microfiltration a washing solution with a pH below the pI value of the protein (pI here pH 8.3) the addition of a positively charged compound leads to a reduction of the loss of protein over the microfiltration retentate.

In a similar experimental setting, the protease was purified by diafiltration of the undiluted fermentation broth without prior removal of the biomass by centrifugation tubular microfiltration membrane with one channel and 6 mm inner diameter. Washing during microfiltration was performed with four volumes of diafiltration washing solution at a transmembrane pressure of 1.3 bar. The diafiltration washing solution was either water, a solution buffered with 10 mM NaHCO3, sodium formiate (NaForm) or NaOAc, or an ultrafiltration permeate (with a conductivity of approximately 17 mS/cm). The pH of the diafiltration washing solution was adjusted as indicated in Table 6. The protease activity of the different fermentation brothes was in the range of 7.4% CV

TABLE 6

| Trial number | Conductivity* [mS/cm] | Mass broth [g] | Diafiltration solution | Diafiltration pH [-] | Retention [%] | Loss over MF-Retentate [%] |
|---|---|---|---|---|---|---|
| 1 | 15.98 | 3000 | water | 7.5 | 55 | 12 |
| 2 | 16.01 | 3000 | water | 7.5 | 51 | 13 |
| 3 | 18.54 | 3273 | buffer (Na Form) | 5.5 | 54 | 13.6 |
| 4 | 17.31 | 3273 | buffer (Na-HCO3) | 9 | 26 | 4.2 |
| 5 | 19.35 | 3273 | Na2SO4 | 5.5 | 33 | 4.5 |
| 6 | 19.28 | 3273 | Na2SO4 | 5.5 | 25 | 3.6 |
| 7 | 20.4 | 3273 | Na2SO4 | 6 | 28 | 4.7 |
| 8 | 20.3 | 2500 | Na2SO4 | 6 | 33 | 5.5 |
| 9 | 18.21 | 2775 | Na2SO4 | 6 | 28 | 4.8 |
| 10 | 21.30 | 3273 | UF-permeate (18.95 mS/cm) | 5.6 | 27 | 4.3 |
| 11 | 18.05 | 3273 | UF-permeate (16.89 mS/cm) | 5.5 | 22 | 3.3 |

* of the fermentation broth

From the data shown in Table 6 it can be derived that washing during the microfiltration step with water or a buffer solution with a pH below the pI value of the protease (pH 8.3) leads to a loss of protease over the microfiltration retentate of approximately 13%. The use of the saline solution leads to a reduced loss of protease over the microfiltration retentate of approximately 4.6%. The use of a washing solution with pH 9.0, i.e., a pH value above the pI value of the protease, leads to a reduced loss of protease over the microfiltration retentate of 4.2%. Instead of a defined washing solution also an ultrafiltration permeate (UF-permeate) with similar conditions yields a reduced loss of protease over the microfiltration retentate of 3.8%.

Thus, the data in Table 6 demonstrates again that when using during microfiltration a washing solution with a pH below the pI value of the protease (pH8.3) the addition of a positively charged compound leads to a reduction of the loss of protein of interest over the microfiltration retentate. In addition, the data in Table 6 show that a similar effect can be achieved by using a washing solution with a pH above the pI value of the protein. In this case, an addition of a positively charged compound is not necessary to achieve this improved protease yield. Furthermore, also process streams, which fulfill the indicated requirements, i.e., a pH value above the pI value of the protein of interest or a pH value below the pI value of the protein of interest, but having a conductivity of between 5-20 mS/cm, can be used as a washing solution.

Example 5

Washing of a Centrifugation Sediment

A protease containing fermentation broth was obtained as described in example 1.

The protease was purified by centrifugation of the fermentation broth in a beaker centrifuge. In one experiment the undiluted fermentation broth was centrifuged and the centrifugation sediment was washed with a washing solution buffered with 10 mM NaOAc having pH 6.0 and comprising a positively charged compound (Na2SO4) up to a conductivity of 15 mS/cm of the washing solution. In another experiment, the fermentation broth was diluted with the same volume of this solution and subsequently centrifuged. The centrifugation sediment was not washed with a washing solution. In both cases the loss of protease over the centrifugation sediment was determined. The protease activity of the different fermentation brothes was in the range of 4.3% CV

TABLE 7

| Trial number | Conductivity* [mS/cm] | Mass broth [g] | Mass pre-dilution solution [g] | Dilution [%] | Mass wash solution [g] | Loss over centrifugation sediment [%] |
|---|---|---|---|---|---|---|
| 1 | 18.6 | 1000 | 21.5 | 2.15 | 1598 | 7.8 |
| 2 | 18.6 | 1000 | 1622 | 162.2 | 0 | 12.9 |

*of the fermentation broth

From the data shown in Table 7 it can be derived that washing the centrifugation sediment with an appropriate washing solution (pH below pI and comprising a positively charged compound) resulted in a loss of protease over the centrifugation sediment of 7.8%. Solely dilution of the fermentation broth with a similar volume of diluent having the same conditions as the washing solution without a subsequent washing step of the centrifugation sediment resulted in a loss of protease over the centrifugation sediment of 12.9%.

Thus, the data in Table 6 demonstrates that simple dilution of the fermentation broth prior separation of the biomass with a washing solution is inferior to a washing step of the centrifugation sediment with respect to loss of protein.

Example 6

Different Complex Nitrogen Sources

A protease containing fermentation broth was obtained by culturing *Bacillus licheniformis* producing a subtilisin protease as described in example 1 using different complex nitrogen sources.

The protease was purified by diafiltration of the undiluted fermentation broth without prior removal of the biomass by centrifugation or other means using a tubular microfiltration membrane with 3 mm inner diameter with one channel and four volumes of diafiltration washing solution at a transmembrane pressure of 1.3 bar. The diafiltration washing solution was buffered with ammonium acetate (NH4OAc) respectively, the pH was adjusted to pH7.5, and conductivity of the washing solution was adjusted with Na2SO4 to 15 mS/cm. No concentration was carried out and four volumes of diafiltration washing solution were applied. The protease activity of the different fermentation brothes was in the range of 2.7% CV.

TABLE 8

| Trial number | Complex N-source | Conductivity* [mS/cm] | Mass broth [g] | T [°C.] | Retention [%] | Loss over MF-Retentate [%] |
|---|---|---|---|---|---|---|
| 1 | Gluten | 22.10 | 3253 | 35 | 17 | 2.7 |
| 2 | Corn steep liquor | 19.79 | 3248 | 35 | 22 | 3.2 |
| 3 | Potato | 18.06 | 5800 | 25 | 32 | 4.9 |
| 4 | Potato | 18.06 | 5800 | 25 | 33 | 1.1 |

*of the fermentation broth

From the data shown in Table 8 it can be derived that with different complex nitrogen sources in the fermentation media, e.g., gluten, corn steep liquor, or potato, a reduced loss of protease over the retentate is achieved when a diafiltration washing solution with a pH value of pH 7.5 (i.e., below the pI value of the protease) and a conductivity of 15 mS/cm is used.

Thus, the data in Table 8 demonstrates that irrespective of the constitution of the fermentation broth a reduction in the loss of protein of interest can be achieved when washing steps are performed using a washing solution with a pH value below the pI value of the protein and the washing solution comprising a positively charged compound.

Example 7

Washing with Water Followed by pH Adjustment Above pI Value

A protease containing fermentation broth was obtained by culturing *Bacillus licheniformis* producing a subtilisin protease as described in example 1. The protease was purified from the fermentation broth by diafiltration. Briefly, the fermentation broth was subjected to microfiltration, wherein the retentate was simultaneously washed with 4 volumes of water. After the second wash volume the pH was adjusted to desorbing conditions by adjusting the pH of the retentate to pH 9. Subsequently the retentate was washed with 2 volumes of water.

As can be seen from the data in Table 9 the adjustment of the conditions during the washing step to desorbing conditions, i.e., to a pH value above the pI value of the protein, lead to low protease losses over the microfiltration retentate.

TABLE 9

| Trial number | Conductivity* [mS/cm] | Mass broth [g] | Diafiltration solution | Loss over MF-Retentate [%] |
|---|---|---|---|---|
| 1 | 8.6 | 8000 | water | 6.7 |
| 2 | 8.7 | 8000 | water | 6.7 |
| 3 | 9.8 | 8000 | water | 5.8 |
| 4 | 10.4 | 8000 | water | 5.4 |
| 5 | 8.8 | 8000 | water | 8.8 |

*conductivity of a fermentation broth

Example 8

Washing with Water Followed by Conductivity Increase

A protease containing fermentation broth was obtained by culturing *Bacillus licheniformis* producing a subtilisin protease as described in example 1. The protease was purified from the fermentation broth by diafiltration. Briefly, the fermentation broth was subjected to microfiltration, wherein the retentate was simultaneously washed with 4 volumes of washing solution, wherein the washing solution was changed during the washing procedure from water to buffer with pH below the pI value of the protein (pH 7.5) and a conductivity of 10 mS/cm $Na_2SO_4$. In trial 3 and 4, the pH of the retentate was adjusted to pH 7.5 and the conductivity was changed to 15 mS/cm after the second washing volume. Subsequently the retentate was washed with 2 volumes of washing solution as indicated in Table 10.

As can be seen from the data in Table 10 the adjustment of the conditions during the washing step to desorbing conditions, in this case to a pH value below the pI value of the protein and the addition of positive cations, lead to low protease losses over the microfiltration retentate.

TABLE 10

| Trial number | Conductivity* [mS/cm] | Mass broth [g] | Diafiltration solution 1 | Diafiltration solution 2 | Diafiltration solution 3 | Diafiltration solution 4 | Loss over MF-Retentate [%] |
|---|---|---|---|---|---|---|---|
| 1 | 15.8 | 3800 | water | water | 10 mM $NH_4$Formate, pH = 7.5 + 10 mS/cm $Na_2SO_4$ | 10 mM $NH_4$Formate, pH = 7.5 + 10 mS/cm $Na_2SO_4$ | 4.0 |
| 2 | 13.5 | 5000 | water | water | 10 mM $NH_4$Formate, pH = 7.5 + 10 mS/cm $Na_2SO_4$ | 10 mM $NH_4$Formate, pH = 7.5 + 10 mS/cm $Na_2SO_4$ | 5.5 |
| 3 | 12.0 | 3000 | water | water | 10 mM $NH_4$Formate, pH = 7.5 + 10 mS/cm $Na_2SO_4$ | 10 mM $NH_4$Formate, pH = 7.5 + 10 mS/cm $Na_2SO_4$ | 6.7 |
| 4 | 8.8 | 4000 | water | water | water | 10 mM $NH_4$Formate, pH = 7.5 + 15 mS/cm $Na_2SO_4$ | 4.9 |

*conductivity of a fermentation broth

The invention claimed is:

1. A method of purifying a protein of interest from particulate matter of a fermentation broth comprising the steps of A) separating the particulate matter from the fermentation broth resulting in a solid portion of the fermentation broth comprising the particulate matter and a liquid portion of the fermentation broth, A2) providing a washing solution comprising one or more conditions that favor solubilization of the protein of interest and/or the desorption of the protein of interest from the particulate matter, wherein one of the conditions comprises:

a) a pH value above the pI value of the protein of interest; or b) a pH value below the pI value of the protein of interest and under these conditions a positively charged compound in a concentration leading to a conductivity of 1-100 mS/cm of the washing solution, and B) conducting one or more washing steps comprising contacting the solid portion of the fermentation broth comprising the particulate matter with a volume of the washing solution to form a resulting solution and removing the same or similar volume of liquid from the resulting solution, whereby the protein of interest is solubilized and/or released from the particulate matter into the resulting solution.

2. The method of claim 1, wherein the step of separating the particulate matter from the fermentation broth is achieved by centrifugation.

3. The method of claim 1, wherein the fermentation broth comprising the protein of interest is diluted prior to the beginning of the purification of the protein of interest.

4. The method of claim 1, wherein the fermentation broth is not diluted prior to the beginning of the purification of the protein of interest.

5. The method of claim 1, wherein an adjustment of pH value of the fermentation broth is performed before the purification of the protein of interest from the biomass of the fermentation broth.

6. The method of claim 1, wherein the conductivity of the fermentation broth is adjusted to a conductivity of 1-100 mS/cm of the fermentation broth by adding an under these conditions positively charged compound before the purification of the protein of interest from the biomass of the fermentation broth.

7. The method of claim 1, wherein one of the conditions of the washing solution that favor the solubilization of the protein of interest and/or the desorption of the protein of interest from the biomass comprises a pH value of the washing solution above the pI value of the protein of interest and the pH value of the washing solution is at least 0.2 pH value units above the pI value of the protein of interest.

8. The method of claim 1, wherein one of the conditions of the washing solution that favor the solubilization of the protein of interest and/or the desorption of the protein of interest from the biomass comprises a pH value of the washing solution below the pI value of the protein of interest and under these conditions a positively charged compound in a concentration leading to a conductivity of 1-100 mS/cm of the washing solution and the pH value of the washing solution is at least 0.2 pH value units below the pI value of the protein of interest.

9. The method of claim 7, wherein the condition that favors the solubilization of the protein of interest and/or the desorption of the protein of interest comprises a pH value of pH 7.0 to pH 13.0.

10. The method of claim 8, wherein the condition of the washing solution that favors the solubilization of the protein of interest and/or the desorption of the protein of interest comprises a pH value of pH 4.0 to pH 9.5 and under these conditions a positively charged compound in a concentration leading to a conductivity of 1-100 mS/cm of the washing solution.

11. The method of claim 8, wherein the positively charged compound is a cation of a salt or wherein the positively charged compound is an amino acid, a peptide or a protein with a pI value above the pI value of the protein of interest, or a combination thereof.

12. The method of claim 1, wherein the purification of the protein of interest from the biomass is achieved by filtration or by centrifugation.

13. The method of claim 1, wherein the purification of the protein of interest from the biomass is achieved by a method selected from the group consisting of cross-flow filtration or dead-end filtration.

14. The method of claim 1, wherein the washing solution comprises at least one solution selected from the group consisting of a buffer solution, a salt solution, a microfiltration filtrate, an ultrafiltration filtrate, centrifugation centrate, water and any other process stream.

15. The method of claim 1, wherein the liquid portion of the fermentation broth after removal of the particulate matter is combined with the one or more washing solutions recovered after washing therewith the solid portion of the fermentation broth.

16. The method of claim 1, wherein the fermentation broth is obtained from the fermentation of a microorganism expressing the protein of interest.

17. The method of claim 16, wherein the microorganism is a prokaryote or a eukaryote.

18. The method of claim 17, wherein the prokaryote is a *Bacillus* cell.

19. The method of claim 1, wherein the protein is an enzyme.

20. The method of claim 19, wherein the enzyme is selected from the group consisting of amylase, protease, lipase, mannanase, phytase, and cellulase.

* * * * *